United States Patent [19]

Banquy

[11] Patent Number: 4,888,130

[45] Date of Patent: Dec. 19, 1989

[54] PROCESS FOR THE PRODUCTION OF SYNTHESIS GAS

[75] Inventor: David L. Banquy, Paris, France

[73] Assignee: Foster Wheeler USA Corporation, Clinton, N.J.

[21] Appl. No.: 161,296

[22] Filed: Feb. 24, 1988

Related U.S. Application Data

[63] Continuation of Ser. No. 502,985, Jun. 10, 1983, abandoned, which is a continuation-in-part of Ser. No. 70,671, Aug. 29, 1979, abandoned, which is a continuation-in-part of Ser. No. 934,075, Aug. 16, 1978, abandoned, which is a continuation-in-part of Ser. No. 810,209, Jun. 27, 1977, abandoned.

[30] Foreign Application Priority Data

Mar. 22, 1977 [FR] France ............................... 77 08459

[51] Int. Cl.$^4$ ............................................. C01B 3/26
[52] U.S. Cl. ............................... 252/373; 48/214 A; 48/215
[58] Field of Search .................. 252/373; 48/196, 197, 48/214 A, 215

[56] References Cited

U.S. PATENT DOCUMENTS

| | | |
|---|---|---|
| 3,264,066 | 8/1966 | Quartulli et al. |
| 3,278,452 | 10/1966 | Vorum . |
| 3,388,074 | 6/1968 | Reitmeier . |
| 3,598,527 | 8/1971 | Quartulli et al. |
| 3,771,261 | 11/1973 | Mandelik et al. |

FOREIGN PATENT DOCUMENTS

2372116  6/1978  France .

Primary Examiner—Howard T. Mars
Attorney, Agent, or Firm—Marvin A. Naigur, Esq.

[57] ABSTRACT

A process starting from a hydrocarbon feedstock, and aiming to produce a synthesis gas suitable either for methanol synthesis or for other applications requiring a low $H_2/CO$ ratio.

In this process, the feedstock, supposed to be desulfurized, is divided into two fractions; a first fraction undergoes a primary steam reforming at high pressure and moderate temperature; the gas effluent from said primary steam reforming, as well as the second fraction of the feedstock, are combined and subsequently undergo a secondary reforming by reaction with an oxygen-containing gas in a reactor operating under essentially adiabatic conditions.

The synthesis gas, obtained as effluent from said secondary reforming, has a composition adjustable at will in a wide range, and therefore can be made as close as necessary to the stoichiometric composition required for methanol synthesis, or it can be made with a low $H_2/CO$ ratio for other applications. The synthesis gas is available at high pressure, and can therefore feed directly, without compression, the synthesis loops downstream.

The process of the present invention is particularly suitable for methanol production on a very large scale.

19 Claims, 1 Drawing Sheet

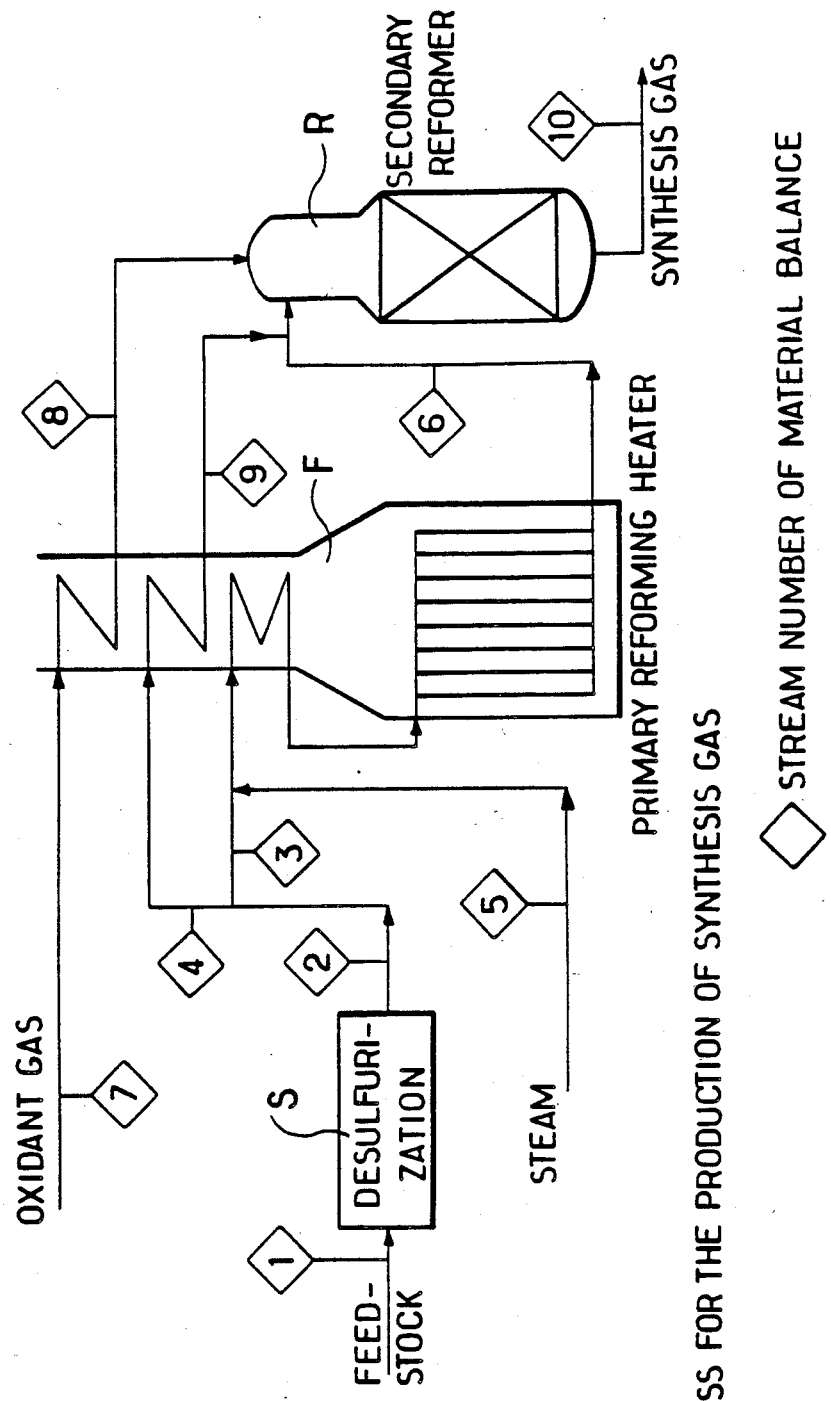

PROCESS FOR THE PRODUCTION OF SYNTHESIS GAS

This application is a continuation of application Ser. No. 502,985 filed June 10, 1983 which is a continuation-in-part of my copending patent application Ser. No. 70,671 filed Aug. 29, 1979, which is a continuation-in-part of my copending application Ser. No. 934,075 filed Aug. 16, 1978, which is a continuation-in-part of my copending patent application Ser. No. 810,209 filed June 27, 1977 all abandoned.

The invention relates to the production of synthesis gas suitable either for methanol synthesis, or for other applications requiring a low $H_2/CO$ ratio.

BACKGROUND OF THE INVENTION

The synthesis of methanol is commercially achieved through a synthesis gas containing hydrogen ($H_2$), carbon monoxide (CO), carbon dioxide ($CO_2$) and small amounts of inert gases such as methane and nitrogen. Carbon oxides react with hydrogen to form methanol according to the following equations:

$$CO + 2H_2 \rightarrow CH_3OH$$

$$CO_2 + 3H_2 \rightarrow CH_3OH + H_2O$$

If $x$, $y$ and $z$ are the molal contents of CO, $CO_2$ and $H_2$ respectively in the synthesis gas, the stoichiometric composition of the latter corresponds to the following relationship:

$$z = 2x + 3y$$

The optimum composition that is usually aimed at is that which leads to the lowest pressure in the methanol synthesis loop for a given production rate, everything else being equal. Said optimum composition can be either identical to the stoichiometric composition, or very slightly different therefrom, because of kinetic reasons connected to the activity and selectivity of the synthesis catalyst, and also due to differences in solubilities of the various reacting gases in liquid methanol.

In the present technology of methanol production starting from a light hydrocarbon feedstock, ranging from natural gas to naphtha, said feedstock is usually first desulfurized and then steam reformed at moderate pressure, in the range of 15 to 25 atm, and at high temperature, in the range of 850° to 900° C. This endothermic reaction is carried out in refractory tubes, externally heated by a set of burners, and filled with a fixed bed of catalyst made essentially of nickel on a refractory support.

Due to the low carbon/hydrogen ratio of such feedstocks and the minimum steam rate which must be used in steam reforming, the synthesis gas produced by such conventional technology has a composition very different from the stoichiometric composition required for methanol synthesis. Said synthesis gas is then cooled and compressed to the pressure used for the methanol synthesis, which ranges from 50 to 100 atm in the so-called "low pressure" processes, and which may reach 300 atm in the older high pressure processes. The synthesis loop operates then with a very large excess of hydrogen, due to the non-stoichiometric composition of the synthesis gas, which leads to a large purge rate from the synthesis loop, the purge gas being generally used as fuel.

The main drawbacks of the above-described conventional processing scheme, of which some are particularly pronounced when a large capacity unit is considered, that is above 2000 metric tons/day of methanol, can be briefly summarized as: (1) a need to purge large quantities of hydrogen from the synthesis loop limits the capacity of the latter; said capacity would be appreciably larger if the synthesis gas had the stoichiometric composition; (2) the low reforming pressure in the synthesis gas preparation, as well as the high purge rate from the synthesis loop, lead to a poor overall efficiency; (3) the high $CO_2$ content of the synthesis gas, as well as the non-stoichiometric composition of the latter, require pressurizing at a very high synthesis gas rate; (4) the horsepower and the dimensions of the synthesis gas compressor become excessive for methanol capacities above 3000 tons/day; (5) the cost of the steam reforming heater, which is a very large fraction of the overall plant cost, increases about linearly with capacity, which means that very little gain can be achieved by scaling up to a large single train capacity; (6) the high $CO_2$ content of the synthesis gas, generally above 10% by volume, produces correlatively important amounts of water in the synthesis loop, thereby increasing the cost of fractioning the methanol-water mixture.

One variation of the above described conventional methanol production scheme consists in adding $CO_2$ upstream or downstream of the steam reforming step, thereby yielding a synthesis gas with a stoichiometric composition. Said variation is interesting only in those cases where the $CO_2$ is available at very low cost from a nearby source. Furthermore, said variation does not avoid the other drawbacks mentioned above, and can be used only in very particular circumstances.

In several applications of synthesis gases for other than methanol production, one has to produce a gas having a high CO content, or a low $H_2/CO$ molal ratio, in the range of 1.5 to 2.5. This is the case for oxo synthesis gas production, pure CO production, and reducing gas production for direct reduction of iron ore for example. As for the case of methanol, it is necessary in the present technology for these cases to operate the steam reforming at high temperature and low pressure; in addition, the synthesis gas produced has a high $H_2/CO$ ratio, due to the minimum steam/hydrocarbon ratio that must be used in the steam reforming process. This situation is partially improved when an outside source of $CO_2$ is available, as mentioned above for the case of methanol.

The main purpose of the present invention is precisely to avoid the above mentioned drawbacks, by producing the synthesis gas at high pressure and with a composition adjustable at will, and in particular equal to the stoichiometric composition required for methanol synthesis, thereby reducing appreciably the equipment sizes in the synthesis loop as well as the need for compression of the synthesis gas, even eliminating entirely said compression in some cases.

Besides the above-described conventional steam reforming process for the production of methanol synthesis gas, a so-called "combination process" could be used, whereby the whole feedstock undergoes first a primary steam reforming reaction, and the resulting effluent then undergoes a secondary reforming with oxygen, in a single stage reactor operating adiabatically and packed with a single catalyst bed. Such a process, as described in U.S. Pat. No. 3,264,066, and also mentioned in U.S. Pat. No. 3,388,074, is essentially that widely used in the ammonia industry in which air is replaced by oxygen. Although said combination process allows the use of higher operating pressures in the synthesis gas generation, it does not lead to a final synthesis gas having the stoichiometric composition required for methanol synthesis or a low $H_2/CO$ ratio, due to the minimum amount of steam that must be used in the primary steam reforming reaction, and for the same reason does not permit a low $CO_2$ content in said synthesis gas.

In U.S. Pat. No. 3,278,452 a process is described for the production of hydrogen and synthesis gases, in which part of the feedstock undergoes a primary steam reforming reaction, and the effluent therefrom is mixed with the other fraction of the feedstock, and the mixture obtained is passed in a secondary reforming reactor through a succession of conversion zones with oxygen introduced between each until the desired conversion is reached. While this process, which is essentially oriented toward the production of hydrogen and ammonia synthesis gas, may to some extent yield a gas approaching the stoichiometric composition required for methanol synthesis, it still leads to a high $CO_2$ content in the synthesis gas and it requires a costly multistage reactor to perform the oxygen reforming reaction, and furthermore the injection of oxygen between the successive catalyst beds, operating at very high temperatures, requires the solution of very elaborate technological problems.

In the foregoing process, the need to use a succession of conversion zones, that is a multistage oxygen reforming reactor, arises from the fact that, due to the high concentration of hydrocarbons in the feed to the secondary reformer, the use of the prior art process, where all the oxygen is introduced in a single step reaction, would lead to carbon formation and excessive temperatures in said secondary reformer, as outlined throughout the aforesaid patent. According to the prior art knowledge, the formation of carbon or carbonaceous material is believed to occur outside a certain temperature range of about 600° to 1500° C., and the excessive temperature is attributed to the hypothetical flame temperature reached by assuming instantaneous reaction of all the oxygen present to produce carbon dioxide and steam, with the total heat of reaction being absorbed as sensible heat by the products of the reaction. Accordingly, in the aforesaid process, the amount of oxygen introduced in each catalyst bed is such that the corresponding flame temperature is below the upper limit of 1550° C. which is believed to be reached on the catalyst, and beyond which carbon formation would occur.

Furthermore, it has been reported in the prior art, as outlined in U.S. Pat. No. 3,278,452, that in a single stage oxygen reforming of a hydrocarbon-containing feedstock, the maximum amount of conversion that may be achieved is such that the percentage methane equivalent of the product gas is about one-fifth of that of the feedstock, when the latter is above 25 percent. The expression "percent methane equivalent" as used herein means mole percent of hydrocarbons expressed as methane on a dry basis, e.g. ten mole percent ethane is 20 percent methane equivalent.

It is an object of the present invention to provide a process in which operation of a single stage secondary oxygen reforming is possible without carbon formation or excessive temperatures, while still achieving a degree of hydrocarbon conversion such that the percentage methane equivalent of the product gas is lower than at least onetenth of that of the inlet feed to said secondary reformer.

Another object of the present invention is to provide a process combining a primary steam reforming with a single stage secondary oxygen reforming, in such a way as to obtain a synthesis gas having essentially the stoichiometric composition required for methanol synthesis, and simultaneously a low $CO_2$ content.

SUMMARY OF THE INVENTION

The present invention relates to a process for producing, from a desulfurized hydrocarbon feedstock, a synthesis gas suitable for methanol synthesis, or for other applications requiring an $H_2/CO$ ratio below 2.5.

In the process of the present invention, the feedstock is divided into two fractions. The first fraction undergoes a primary steam reforming reaction at high pressure and mild temperature. The gas effluent from said reaction, as well as the second fraction of the feedstock, are combined and subsequently undergo jointly a secondary reforming reaction in an adiabatic reactor by reacting with an oxygencontaining gas.

The same or different, commercially available, or prior art, catalysts can be used for the primary and secondary reforming steps. Nickel oxide is particularly useful as the active component of the catalyst although iron oxide, cobalt oxide, chromia, molybdena and tungsten oxide also can be used as the active component. The active component may be supported on a refractory support such as aluminum oxide, an alkaline earth oxide, zirconium oxide or a combination thereof. A promoter can be included in the catalyst, including thorium, cerium, cesium, an alkaline oxide, or combination thereof.

The synthesis gas obtained as effluent from said secondary reforming has a composition adjustable at will in a wide range, and therefore can be made as close as necessary to the stoichiometric composition required for methanol synthesis, or it can be made having a low $H_2/CO$ ratio for other applications, and this synthesis gas is available at high pressure and can therefore be fed directly, without compression, to the synthesis loops downstream.

The process of the present invention is particularly suitable for methanol production on a very large scale.

DESCRIPTION OF THE PREFERRED EMBODIMENTS

Any feedstock which can undergo a steam reforming reaction can be used as feedstock in the process of the present invention. In the frame of the present technology, the feedstocks which can be steam reformed are essentially composed of light hydrocarbons ranging from methane to a naphtha having an end point of about 220° C.

The main objective of the process of the present invention is to produce, under high pressure, a synthesis gas having either a composition very close or equal to the stoichiometric composition required for methanol synthesis, or an $H_2/CO$ ratio below 2.5, which is lower than what would be possible to achieve by plain steam reforming.

It is well known that steam reforming of the total process feedstock requires on one hand a minimum steam rate, which leads to an excess of hydrogen in the synthesis gas produced, and on the other hand a very high temperature to reduce the amount of residual methane, thereby limiting the operating pressure to a low or medium level.

Oxygen reforming is another industrial reaction widely practiced in the process industries for many years for the production of synthesis gases at pressures ranging from 8 to 25 atm. The oxygen-containing gas used in this reaction is either oxygen, or oxygen enriched air, or even air such as in the case of ammonia production. The feedstock used in such reaction is either a hydrocarbon mixture such as natural gas, liquefied petroleum gases or naphtha, or partially steam reformed hydrocarbons as used in the case of ammonia production. Said oxygen reforming reaction is carried out industrially in a refractory lined reactor, operating under essentially adiabatic conditions, and containing a single bed of one or several catalysts, designed to resist the high temperatures prevailing in the reactor. Specifically, a fixed bed of nickel based catalyst is used.

The process of the present invention combines the steam reforming reaction with the oxygen reforming reaction, in a way which allows the operation at high pressure, and the use of a low overall steam rate per unit of total feedstock, that is lower than what would be possible by plain steam reforming, thereby producing a synthesis gas having either the stoichiometric composition required for methanol synthesis, or an $H_2/CO$ ratio below 2.5 for other applications.

The present invention is primarily concerned with a process of producing synthesis gas in which a hydrocarboncontaining feedstock is first split into two feedstock fractions or streams, one fraction is subjected to a primary steam reforming, the resulting gaseous effluent is combined with the second feedstock fraction to form a mixture, and the mixture is then reacted with an oxygen containing gas in a secondary reforming reactor. The greatest advance is primarily in the method of effecting the reaction in the secondary reforming reactor. However, the invention is also concerned with the overall process which employs novel procedures and conditions of reaction.

According to one aspect of the invention there is provided a process for producing, from a desulfurized hydrocarbon-containing feedstock, a synthesis gas having essentially the stoichiometric composition required for methanol synthesis and low $CO_2$ content, in which after, (a) dividing said feedstock into two fractions, the first fraction representing about 30 to 66.7 percent of the total feedstock, (b) subjecting the first fraction from (a) to a primary steam reforming reaction under a high pressure, by mixing said fraction with steam, and heating the mixture thereof by indirect heat exchange, in the presence of a reforming catalyst, to form a gaseous effluent including hydrogen, (c) preheating the second fraction from (a), by indirect heat exchange and mixing said fraction with the gas effluent from (b), (d) combining effluent gas streams from (b) and (c) to obtain a gas mixture at a minimum temperature of 600° C. and containing a minimum of 35 percent methane equivalent, and (e) preheating a free oxygen-rich gas to a temperature above 350° C. by indirect heat exchange, the gas mixture from (d) is reacted in a single step with the oxygen rich gas from (e) in a secondary reforming reactor operating under essentially adiabatic conditions, and comprising a gas mixing zone and a reaction zone, the amount of free oxygen injected in said mixing zone being sufficient to initiate therein the partial oxidation reaction, and the mixing of the reacting gases in said mixing zone being accomplished through a mixing apparatus designed to obtain quasiinstantaneously a homogeneous mixture before the exothermic partial oxidation reaction proceeds significantly, and with said reaction zone containing a single ted of catalyst or catalysts, thus producing a synthesis gas containing a percent methane equivalent of less than one-tenth of that of the gas mixture from (d), a $CO_2$ content of less than 8 percent by volume, and CO, $CO_2$ and $H_2$ in a stoichiometric ratio for methanol synthesis.

According to another aspect of the invention there is provided a process for producing, from a desulfurized hydrocarbon-containing feedstock, a synthesis gas having a molal $H_2/CO$ ratio below 2.5, in which after, (a) dividing said feedstock into two fractions, the first fraction representing about 5 to 40 percent of the total feedstock, (b) subjecting the first fraction from (a) to a primary steam reforming reaction under a high pressure, by mixing said fraction with steam, and heating the mixture thereof by indirect heat exchange, in the presence of a reforming catalyst, to form a gaseous effluent including hydrogen, (c) preheating the second fraction from (a), by indirect heat exchange, and mixing said fraction with the gas effluent from (b), (d) combining effluent gas streams from (b) and (c) to obtain a gas mixture at a minimum temperature of 600° C. and containing a minimum of 35 percent methane equivalent, and (e) preheating a free oxygen-rich gas to a temperature above 350° C. by indirect heat exchange, the gas mixture from (d) is reacted in a single step with the oxygen-rich gas from (e) in a secondary reforming reactor operating under essentially adiabatic conditions, and comprising a gas mixing zone and a reaction zone, the amount of free oxygen injected in said mixing zone being sufficient to initiate therein the exothermic partial oxidation reaction which raises the temperature of the reaction mixture, and the mixing of the reacting gases in said mixing zone being accomplished through a mixing apparatus designed to obtain quasi-instantaneously a homogeneous mixture before the partial oxidation reaction proceeds significantly, and said reaction zone containing a single bed of catalyst or catalysts, thus producing a synthesis gas containing a percent methane equivalent of less than one-tenth of that of the gas mixture from (d) and a molal $H_2/CO$ ratio below 2.5.

BRIEF DESCRIPTION OF THE DRAWING

The drawing represents a simplified schematic flow diagram of the improved process of the present invention in its preferred form.

It is well known that all the catalytic processes, whether steam or oxygen reforming, for the production of synthesis gases from a hydrocarbon feedstock, require that said feedstock be thoroughly desulfurized prior to the synthesis gas generation step. Therefore, the feedstock is supposed to be adequately desulfurized for the purpose of the present invention, which is symbolized by step S of the drawing.

In the process of the present invention, the desulfurized feedstock is brought to the reforming pressure, by compression or by pumping, either before or after the desulfurization step S. Due to the moderate temperatures used in the steam reforming heater F, it is advantageous to operate at a high pressure, desirably at 15 atm or above. In the most interesting applications of the present invention, it will be found advantageous to operate at a pressure of above 40, and even at about 50 to 120 atm.

After compression, the feedstock, stream 2 on FIG. 1, is then divided into two fractions. The first fraction, stream 3, undergoes a primary steam reforming reaction in reforming heater F. Said fraction is mixed with a certain amount of steam corresponding to stream 5 on the drawing, and the mixture is injected in the reforming tubes at a temperature generally between about 400° to 600° C.

The amount of steam used in the aforesaid primary steam reforming reaction is generally expressed by the ratio of the number of moles of $H_2O$ to the number of carbon atoms contained in the hydrocarbons of that feedstock fraction undergoing the steam reforming reaction, said ratio being commonly known as the steam/carbon ratio. Depending on the elemental composition of the feedstock and the application contemplated for the synthesis gas, it is possible to use, in the process of the present invention, a wide range of steam/carbon ratios, extending from 1.2 to 5.0. Furthermore, the operating pressure, and/or the activity and selectivity of the catalysts used, may affect the choice of this ratio.

The endothermic reaction which takes place inside the reforming tubes, on contact with the catalyst, converts the reacting gases into a gas mixture containing hydrogen, carbon oxides, methane and a small amount of ethane, with all the other hydrocarbons being completely converted. The heat required for said endothermic reaction is supplied by the burners of primary reforming heater F.

One of the main features in the process of the present invention is that the temperature of the process gas effluent from the primary steam reforming is very moderate, generally being between 700° and 850° C., and preferably between 750° and 820° C., this being precisely the reason by which it is possible to operate at a high pressure of 15 atm or above, and pressures appreciably higher than 40 atm, while still using reforming tubes made of the same refractory alloys as presently used in commercial practice. As a consequence, the residual methane content in the gas effluent from primary steam reformer or heater F is comparatively high, that is above 10 percent by volume on a dry basis, and such that by mixing it with the other fraction of the feedstock, stream 4, in the subsequent step, the mixture thereof contains at least 35 percent of methane equivalent.

The following step in the process of the present invention is a single step secondary oxygen reforming, in which at least the following three streams are reacted jointly: (a) the gas effluent from the preceding primary steam reforming, stream 6 on the drawing, which is injected in secondary reformer R without a change in temperature; (b) the second or other fraction of the feedstock, stream 4, which has not undergone any reforming reaction yet, and which is preheated to a temperature higher than 350° C. by indirect heat exchange and then mixed with stream 6 before contacting the oxygen rich gas; (c) a free oxygen-rich gas, stream 7, having a total content of nitrogen and rare gases below 20 percent by volume, and preferably below 5 percent by volume, and preheated to a temperature above 350° C., and preferably above 400° C., by indirect heat exchange.

The secondary reformer R in the present invention is similar to those presently used industrially and described above; it is essentially composed of a gas mixing zone, where the reacting gases are first contacted, and a reaction zone which contains a single nickel catalyst bed, although said catalyst bed may contain two or more layers of different catalysts. One of the features of the present invention is that the amount of free oxygen injected in a single step through stream 7, in order to achieve the degree of hydrocarbon conversion required, is such that the partial oxidation reaction will be initiated in the gas mixing zone of reactor R at the point of contact between the oxygen stream and the mixture of streams 6 and 9.

It should be noted that the conditions of the reacting gases in the gas mixing zone of reactor R, in the present invention, are much more severe than those presently practiced in the synthesis gas industry. This is so because the oxygen concentration in the mixture is much higher, because the hydrocarbons content in the feed is much higher, namely above 35 percent methane equivalent, because the hypothetical flame temperature is higher than 1550° C., and furthermore because the mixture of streams 6 and 9 may contain hydrocarbons heavier than methane. As is known in the prior art, and mentioned above, there is a risk of carbon formation and excessive temperatures under such severe conditions.

In the concept underlying the present invention, such carbon formation, when it occurs, is tied to the kinetics of the reactions by the fact that the oxygen reaction rate with hydrogen and hydrocarbons is very high compared to that at which the reacting gases are mixed together. Therefore, if the reaction is proceeding significantly while the mixture is still very heterogeneous, those fractions having a great excess of oxygen will reach very high temperatures, and the other fractions, very deficient in oxygen, will be subjected to thermal cracking, leading to carbon formation in the temperature range of 400° to about 600° C., the endothermic heat of reaction of said thermal cracking being transmitted by radiation from the high temperature fractions. According to this concept, although the hypothetical flame temperature is higher than 1550° C., such risks of carbon formation and excessive temperatures are obviated on one hand by setting minimum temperature limitations on the reacting gases at the inlet of the secondary reformer, and on the other hand by injecting the reacting gases to said reformer through a mixing apparatus designed to obtain quasi instantaneously a homogeneous mixture before the partial oxidation reaction proceeds significantly. One such apparatus is disclosed in my copending patent application Ser. No. 950,850 filed Oct. 12, 1978, now abandoned, which is entirely incorporated herein by reference. That apparatus is also disclosed in my Canadian patent 1,116,856 issued Jan. 26, 1982 and my French patent 2,407,738 granted July 9, 1982. The French patent, the Canadian patent and the said abandoned U.S. application all were based on, and claimed priority from, the application which resulted in the French patent. For this reason, the contents of the said abandoned U.S. application is not physically incorporated in this specification. However, other apparatus can be suitably employed. Prior art apparatus for the intended purpose is referred to in that patent application.

Accordingly, in the process of the present invention, an essential requirement for obviating the risk of carbon formation in secondary reformer R is by setting the following minimum temperature limitations on the reacting gases at the inlet of said reformer: (a) the gas effluent from primary reformer F, stream 6, should be at a minimum temperature of 700° C. as stated above, (b)

the second fraction of the feedstock, stream 9, should be preheated to a temperature such that, after mixing with stream 6 from primary reformer F, the mixture thereof is at a minimum temperature of 600° C., and (c) the free oxygen-rich gas, stream 8, should be preheated to a minimum temperature of 350° C.

The above temperature limitations are also intended to help achieve, in the final synthesis gas, either the stoichiometric composition required for methanol synthesis, or an $H_2/CO$ ratio below 2.5, while keeping a low $CO_2$ content in said gas.

The preheating of streams 4 and 7 can preferably be achieved in the convection section of primary reformer F, as shown on the drawing.

Under all circumstances, gas streams 6 and 9 should be thoroughly mixed together before contacting oxygen stream 8; this can be achieved either in a line outside reactor R, or in the gas mixing zone inside the reactor, as shown on the drawing. The mixture of streams 6 and 9 is subsequently contacted with oxygen stream 8 in the gas mixing zone of secondary reformer R, through a mixing apparatus designed to disperse the oxygen in the other reacting gas mixture at a rate comparable or higher than that of the oxygen reaction with hydrogen and hydrocarbons, thereby obtaining quasiinstantaneously a homogeneous gas mixture before the partial oxidation reaction proceeds significantly.

The overall exothermic reaction which takes place in secondary reformer R raises appreciably the temperature of the reacting gas mixture, to a level comprised between 900° and 1200° C., and preferably between 960° and 1100° C. The oxygen disappears entirely in the course of the reaction, and the synthesis gas thus produced, stream 10 on the drawing, contains a small amount of residual methane, less than five percent, and preferably less than three percent, by volume on a dry basis, the lower methane content being desirable to limit the amount of purge gas in the methanol synthesis loop, or in other similar synthesis loops. In any case, this residual methane percentage, or the percent methane equivalent, is less than one-seventh of the percent methane equivalent of the feed to the secondary reformer, and preferably less than one-tenth of the percent methane equivalent of said feed.

The catalysts used in the primary steam reformer F and the secondary oxygen reformer R can be any ones of the conventional catalysts presently used in commercial practice for the production of synthesis gases from hydrocarbons. Said conventional catalysts usually contain one or more of the following active components: nickel, nickel oxide, cobalt oxide, chromia and molybdenum oxide. The active component may be supported on a refractory support such as aluminum oxide, an alkaline earth oxide, zirconium oxide, or a combination thereof. A promoter can be included in the catalyst, including thorium, cerium, cesium, an alkaline oxide, or combination thereof. The composition and method of preparation of the catalysts used in reducing the present invention to practice form no part of this invention. However, the following U.S. patents disclose more information on catalysts useful in the invention: Nos. 3,264,066; 3,442,613; 3,763,205; 4,079,017. "Catalyst Handbook" 1970, Wolfe Scientific Books, London, Chapter 5, pages 64–96 and "Steam Reforming Catalysts" by J. R. Rostrup-Nielsen, 1975, Teknisk Forlag A/S, Copenhagen, Chapter 2, pages 38–48, disclose further information on the conventional catalysts useful in the invention.

The reduction to practice of the present invention must take into account al the principal parameters that have an effect on the final synthesis gas composition, namely: the elemental composition of the feedstock, the split of the feedstock between the first and second fractions, the steam/carbon ratio used in the primary steam reforming, the operating pressure of the primary and secondary reformings, the outlet temperatures of the primary and secondary reformings, the oxygen rich-gas rate used in the secondary reforming, and the preheat temperatures of the gas streams to the secondary reformer.

In general, to obtain in the final synthesis gas 10 and $H_2/CO$ ratio below 2.5, the first fraction 3 of the feedstock should be small, for example comprised between 5 and 40 percent of the total feedstock 2. The steam/carbon ratio should be as low as possible, in accordance with the activity and selectivity of the catalyst.

When producing a methanol synthesis gas, one is aiming on one hand to obtain a stoichiometric gas composition, and on the other hand to have a $CO_2$ content in the final gas equal to the minimum compatible with the methanol synthesis process used downstream. In the low pressure methanol synthesis processes, said minimum $CO_2$ content is in the range of 3 to 8 percent by volume, and this is a controlling factor in selecting the steam/carbon ratio in the primary steam reforming, and the relative split of the feedstock between the two fractions.

The elemental composition of the feedstock is also an important factor in the split of the total feedstock between the first and second fractions. In this regard, the higher the C/H ratio of the feedstock, the larger will be the first fraction or stream 3. In the case of a synthesis gas for methanol production, said fraction may vary between 30 and 95 percent of the total feedstock.

Finally, the selection of the process parameters depends also to a large extent upon economic conditions, for example upon the relative prices of oxygen and fuel.

In Table I below, there are set forth five typical examples of application of the present invention, each one being identified by the corresponding main process parameters, and by the effluent gas compositions from the two reforming steps. In all these examples, the feedstock is considered to be pure methane, which has the lowest C/H ratio of all the hydrocarbons, and therefore is the most difficult to convert into a synthesis gas having either a stoichiometric composition for methanol synthesis, or a low $H_2/CO$ ratio for the other applications mentioned above. The gas streams in Table I have the same reference numbers as those on the drawing. The data in Table I is based on the use of any conventional nickel catalysts, in the primary and secondary reforming process steps.

TABLE I
EXAMPLES OF APPLICATION

| | CASE 1 | CASE 2 | CASE 3 | CASE 4 | CASE 5 |
|---|---|---|---|---|---|
| TOTAL $CH_4$ rate ⟨2⟩ Kg.mol/h | 8753.21 | 8704.06 | 9322.93 | 9052.30 | 600 |
| REFORMING pressure atm. abs. | 49.3 | 69 | 49.3 | 69 | 49.3 |
| PRIMARY STEAM REFORMING | | | | | |
| Inlet $CH_4$ rate ⟨3⟩ Kg.mol/h | 4376.60 | 4352.03 | 5327.39 | 6034.87 | 100 |
| Inlet $H_2O$ rate ⟨5⟩ Kg.mol/h | 10503.85 | 12185.68 | 18645.85 | 19915.07 | 240 |
| Steam/carbon ratio | 2.4 | 2.8 | 3.5 | 3.3 | 2.4 |
| Effluent gas ⟨6⟩ : $H_2O$ Kg.mol/h | 7846.68 | 9569.33 | 14508.34 | 15870.20 | 179.287 |
| $H_2$ Kg.mol/h | 5951.31 | 5756.08 | 9133.16 | 8851.10 | 135.980 |
| CO Kg.mol/h | 636.97 | 523.37 | 858.19 | 761.30 | 14.554 |
| $CO_2$ Kg.mol/h | 1010.12 | 1046.49 | 1639.66 | 1641.79 | 23.080 |
| $CH_4$ Kg.mol/h | 2729.56 | 2782.17 | 2829.53 | 3631.78 | 62.367 |
| Total | 18174.64 | 19677.44 | 28968.88 | 30756.17 | 415.268 |
| Temperature °C. | 760 | 760 | 760 | 760 | 760 |
| SECONDARY REFORMING | | | | | |
| Inlet $CH_4$ rate ⟨4⟩ Kg.mol/h | 4376.60 | 4352.03 | 3995.54 | 3017.43 | 500 |
| Inlet oxident rate ⟨7⟩ : $O_2$ Kg.mol/h | 3906.24 | 3906.24 | 3906.24 | 3906.24 | 307.655 |
| $N_2$ Kg.mol/h | 19.63 | 19.63 | 19.63 | 19.63 | 1.546 |
| Effluent gas ⟨10⟩ : $H_2O$ Kg.mol/h | 8473.19 | 10118.34 | 15063.45 | 16551.17 | 236.367 |
| $H_2$ Kg.mol/h | 18620.70 | 18319.35 | 21442.25 | 20655.12 | 1149.833 |
| CO Kg.mol/h | 6746.89 | 6372.11 | 6464.89 | 6114.71 | 527.258 |
| $CO_2$ Kg.mol/h | 1548.14 | 1753.87 | 2 465.03 | 2530.84 | 45.843 |
| $CH_4$ Kg.mol/h | 458.19 | 578.04 | 393.00 | 406.75 | 26.90 |
| $N_2$ Kg.mol/h | 19.63 | 19.63 | 19.63 | 19.63 | 1.546 |
| Temperature °C. | 1060 | 1066 | 1027 | 1049 | 1149 |
| RATIO $H_2/2(CO) + 3(CO_2)$ | 1.027 | 1.017 | 1.055 | 1.042 | — |
| METHANOL PRODUCTION (approx.) T/d | 6124 | 5999 | 6592 | 6383 | — |

Cases 1 and 2 of Table I correspond to the production of methanol synthesis gas suitable for a low or medium pressure methanol synthesis process, designed to operate with a comparatively low $CO_2$ content in the feed gas.

Cases 3 and 4 of Table I correspond to the production of methanol synthesis gas suitable for a low pressure methanol synthesis process requiring a comparatively higher $CO_2$ content in the feed gas.

The material balances of cases 1, 2, 3 and 4 in Table I are based on an oxygen consumption of 3000 metric tons/day, which represents about the largest single train oxygen production unit that can be considered presently. It is then realized that the corresponding methanol capacity is equal to or higher than 6,000 metric tons/day in all these cases. Thus, the process of the present invention makes it possible to build such a capacity in a single train plant, while using on one hand a synthesis gas compressor of a reasonable horsepower, and possibly deleting completely the need for said compressor due to the high pressure at which the gas is available, and on the other hand a steam reforming heater of a size comparable to the largest heaters presently in operation. In addition, said reforming heater in the present invention represents a much smaller fraction of the overall investment cost, and therefore the advantage of scaling up becomes very appreciable, as the other equipment items of the methanol plant have a low cost versus capacity exponent.

Case 5 of Table I corresponds to other applications than methanol synthesis, when a $H_2/CO$ ratio below 2.5 is needed. It should be noted that the production of a synthesis gas with a low $H_2/CO$ ratio leads correlatively to a high $(H_2+CO)$ content, by virtue of chemical equilibrium, and this is also an important objective in the production of reducing gases for the direct reduction of iron ore.

It should also be noted that in the five examples given above in Table I, the percent methane equivalent in the feed to the secondary reformer ranges from 37 to 76 percent, whereas the percent methane equivalent in the effluent of said reformer ranges from 1.3 to 2.2 percent. Therefore, the percent methane equivalent has been reduced by a factor of 23 to 49 through the secondary reformer. Such a degree of hydrocarbon conversion would not be achieved in a single stage reaction using the prior art processes.

All the material balances of Table I are based on the following assumptions: (a) the oxygen rich gas contains 99.5 volume percent oxygen and 0.5 volume percent ($N_2+A$), and said gas is preheated to 650° C. prior to injection in reactor R; (b) fraction 4 of the feedstock is also preheated to 650° C. prior to injection in reactor R; (c) the presence of ethane is neglected in the effluents from the primary and secondary reformings; (d) the approach to equilibrium for the CO shift conversion reaction equals zero for the primary and secondary reformers; and (e) the approach to equilibrium for the steam-methane reaction equals 13° C. for the primary reformer, and is equal to 9° C. for the secondary reformer. Said approach to equilibrium, as known in the industry, is defined for each chemical reaction as the difference between the actual gas temperature and the fictitious temperature corresponding to the actual gas composition.

The approaches to equilibrium assumed in the data of Table I are commonly achieved in industrial practice, using the conventional nickel based reforming catalysts. Thus, the operating conditions given in Table I can be achieved by using in the primary reformer F, and the secondary reformer R, any one of the conventional nickel based catalysts presently used in the synthesis gas industry, as long as the volume of catalyst for each case of Table I and for each reforming operation is sufficient to meet the approaches to equilibrium assumed in Table I and reported above.

There are several ways to reduce to practice the present invention when two or several feedstocks are to be used simultaneously. For example, one can either mix the feedstocks at the start, partially or completely, and then proceed with the split between fractions 3 and 4 as described above, or one can select one or two of said feedstocks to be steam reformed in the primary steam reforming step, and then inject all the other feedstocks directly into the secondary reforming step. These various means of combining the feedstocks, although not represented in the aforesaid material balances, are within the spirit of the present invention, which is based on an original combination of processing steps, said combination offering the same advantages whatever number and combination of feedstocks are used.

While particular embodiments of the present invention have been described, it will be understood, of course, that this invention is not limited thereto since many modifications may be made, and it is therefore contemplated to cover by the appended claims any and all such modifications as may fall within the true spirit and scope of this invention.

What I claim is:

1. A process for producing, from a desulfurized hydrocarbon-containing feedstock, a synthesis gas having essentially the stoichiometric composition required for methanol synthesis and low $CO_2$ content, consisting essentially of:
   (a) dividing said feedstock into two fractions, the first fraction representing 30 to 95 percent of the total feedstock,
   (b) subjecting the first fraction from (a) to a primary steam reforming reaction under a pressure higher than 40 atmospheres, by mixing said fraction with steam, and heating the mixture thereof by indirect heat exchange, in the presence of a reforming catalyst, to form a gaseous effluent including hydrogen at a temperature between 700° and 850° C.,
   (c) preheating the second fraction from (a), by indirect heat exchange, to a temperature such that, after mixing said fraction with the gas effluent from (b) in the subsequent step, the mixture thereof is at a minimum temperature of 600° C.,
   (d) combining effluent gas streams from (b) and (c) to obtain a gas mixture at a minimum temperature of 600° C. and containing a minimum of 35 percent methane equivalent,
   (e) preheating a free oxygen-rich gas to a temperature above 350° C. by indirect heat exchange,
   (f) reacting in a single step the gas mixture from (d) with the oxygen rich gas from (e) in a single stage secondary reforming reactor operating under essentially adiabatic conditions, and consisting essentially of a gas mixing zone and a reaction zone, the total amount of free oxygen injected in said mixing zone constitutes the total amount of free oxygen supplied for reaction with the combined effluent gas stream mixture from (d) to produce the synthesis gas and being sufficient to initiate therein the partial oxidation reaction, and the mixing of the reacting gases in said mixing zone being accomplished through a mixing apparatus designed to obtain quasiinstantaneously a homogeneous mixture before the partial oxidation reaction proceeds significantly, and said reaction zone containing a single bed of catalyst or catalysts, whereby the total homogeneous mixture is passed only once through the whole catalyst bed thus producing a synthesis gas containing a percent methane equivalent of less than one-tenth of that of the gas mixture from (d), and a $CO_2$ content of less than 8 percent by volume.

2. A process according to claim 1, wherein the effluent gas temperature from the primary steam reforming step (b) is between 750° and 820° C.

3. A process according to claim 1 or 2, wherein the effluent gas temperature from the secondary oxygen reforming step (f) is between 900° and 1200° C.

4. A process according to claim 1 or 2, wherein the free oxygen-rich gas used in the secondary reforming contains less than 5 percent by volume of nitrogen and rare gases.

5. A process according to claim 1 or 2, wherein the operating pressure of the primary steam reforming and the secondary oxygen reforming is between 40 and 120 atm.

6. A process according to claim 1 or 2, wherein the ratio between the number of steam moles used in the primary steam reforming to the number of hydrocarbon carbon atoms treated in said primary steam reforming is between about 1.2 and 5.0.

7. A process for producing, from a desulfurized hydrocarbon containing feedstock, a synthesis gas having a molal $H_2/CO$ ratio below 2.5, consisting essentially of:
   (a) dividing said feedstock into two fractions, the first fraction representing 5 to 40 percent of the total feedstock,
   (b) subjecting the first fraction from (a) to a primary steam reforming reaction under a pressure higher than 40 atmospheres, by mixing said fraction with steam, and heating the mixture thereof by indirect heat exchange, in the presence of a reforming catalyst, to form a gaseous effluent including hydrogen at a temperature between 700° and 850° C., (c) preheating the second fraction from (a), by indirect heat exchange, to a temperature such that, after mixing said fraction with the gas effluent from (b) in the subsequent step, the mixture thereof is at a minimum temperature of 600° C., (d) combining effluent gas streams from (b) and (c) to obtain a gas mixture at a minimum temperature of 600° C. and containing a minimum of 35 percent methane equivalent, (e) preheating a free oxygen-rich gas to a temperature above 350° C. by indirect heat exchange, (f) reacting in a single step the gas mixture from (d) with the oxygen-rich gas from (e) in a secondary reforming reactor operating under essentially adiabatic conditions, and consisting essentially of a gas mixing zone and a reaction zone, the total amount of free oxygen injected in said mixing zone constituting the total amount of free oxygen supplied in the process for reaction with the combined effluent gas stream mixture from (d) to produce the synthesis gas and being sufficient to initiate therein the partial oxidation reaction, and the mixing of the reacting gases in said mixing zone being accomplished through a mixing apparatus designed to obtain quasi-instantaneously a homogenous mixture before the partial oxidation reaction proceeds significantly, and said reaction zone containing a single bed of catalyst or catalysts, whereby the total homogeneous mixture is passed only once through the whole catalyst bed thus producing a synthesis gas containing a percent methane equivalent of less than one-tenth of that of the gas mixture from (d).

8. A process according to claim 7, wherein the effluent gas temperature from the primary steam reforming step (b) is between about 750° and 820° C.

9. A process according to claim 7 or 8, wherein the effluent gas temperature from the secondary oxygen reforming step (f) is between about 900° and 1200° C.

10. A process according to claim 7 or 8, wherein the free oxygen-rich gas used in the secondary reforming contains less than 5 percent by volume of nitrogen and rare gases.

11. A process according to claim 7 or 8, wherein the operating pressure of the primary steam reforming and the secondary oxygen reforming is between 40 and 120 atm.

12. A process according to claim 7 or 8, wherein the ratio between the number of steam moles used in the primary steam reforming to the number of hydrocarbon carbon atoms treated in said primary steam reforming is between 1.2 and 5.0.

13. A process for producing, from a desulfurized hydrocarbon-containing feedstock, a synthesis gas having essentially the stoichiometric composition required for methanol synthesis and low $CO_2$ content, consisting essentially of:

(a) dividing said feedstock into two fractions, the first fraction representing 30 to 66.7 percent of the total feedstock, (b) subjecting the first fraction from (a) to a primary steam reforming reaction under a high pressure, by mixing said fraction with steam, and heating the mixture thereof by indirect heat exchange, in the presence of a reforming catalyst, to form a gaseous effluent including hydrogen to a temperature at or above 700° C., (c) preheating the second fraction from (a), by indirect heat exchange, to a temperature such that, after mixing said fraction with the gas effluent from (b) in the subsequent step, the mixture thereof is at a minimum temperature of 600° C., (d) combining effluent gas streams from (b) and (c) to obtain a gas mixture at a minimum temperature of 600° C. and containing a minimum of 35 percent methane equivalent, (e) preheating a free oxygen-rich gas to an elevated temperature above 350° C. by indirect heat exchange, (f) reacting in a single step the gas mixture from (d) with the oxygen rich gas from (e) in a secondary reforming reactor operating under essentially adiabatic conditions, and consisting essentially of a gas mixing zone and a reaction zone, the total amount of free oxygen injected in said mixing zone constituting the total amount of free oxygen supplied in the process for reaction with the combined effluent gas stream mixture from (d) to produce the synthesis gas and being sufficient to initiate therein the exothermic partial oxidation reaction which raises the temperature of the reaction mixture, and the mixing of the reacting gases in said mixing zone being accomplished through a mixing apparatus designed to obtain quasi-instantaneously a homogeneous mixture before the partial oxidation reaction proceeds significantly, and with said reaction zone containing a single bed of catalyst or catalysts, whereby the total homogeneous mixture is passed only once through the whole catalyst bed thus producing a synthesis gas containing a percent methane equivalent of less than one-tenth of that of the gas mixture from (d), a $CO_2$ content of less than 8 percent by volume, and CO, $CO_2$, and $H_2$ in essentially a stoichiometric ratio for methanol synthesis.

14. A process for producing, from a desulfurized hydrocarbon containing feedstock, a synthesis gas having a molal $H_2/CO$ ratio below 2.5, consisting essentially of:

(a) dividing said feedstock into two fractions, the first fraction representing 5 to 40 percent of the total feedstock, (b) subjecting the first fraction from (a) to a primary steam reforming reaction under a high pressure, by mixing said fraction with steam, and heating the mixture thereof by indirect heat exchange, in the presence of a reforming catalyst, to form a gaseous effluent including hydrogen at a temperature at or above 700° C., (c) preheating the second fraction from (a), by indirect heat exchange, to a temperature such that, after mixing said fraction with the gas effluent from (b) in the subsequent step, the mixture thereof is at a minimum temperature of 600° C., (d) combining effluent gas streams from (b) and (c) to obtain a gas mixture at a minimum temperature of 600° C. and containing a minimum of 35 percent methane equivalent, (e) preheating a free oxygen-rich gas to an elevated temperature above 350° C. by indirect heat exchange, (f) reacting in a single step the gas mixture from (d) with the oxygen rich gas from (e) in a secondary reforming reactor operating under essentially adiabatic conditions, and consisting essentially of a gas mixing zone and a reaction zone, the amount of free oxygen injected in said mixing zone constituting the total amount of free oxygen supplied in the process for reaction with the combined effluent gas stream mixture from (d) to produce the synthesis gas and being sufficient to initiate therein the exothermic partial oxidation reaction which raises the temperature of the reaction mixture, and the mixing of the reacting gases in said mixing zone being accomplished through a mixing apparatus designed to obtain quasi-instantaneously a homogeneous mixture before the partial oxidation reaction proceeds significantly, and said reaction zone containing a single bed of catalyst or catalysts, whereby the total homogeneous mixture is passed only once through the whole catalyst bed thus producing a synthesis gas containing a percent methane equivalent of less than one-tenth of that of the gas mixture from (d) and a molal $H_2/CO$ ratio below 2.5.

15. A process according to claim 13 or 14 in which the percent methane equivalent in the feed to the secondary reformer ranges from 37 to 76 percent, and the percent methane equivalent in the effluent of said reformer ranges from 1.3 to 2.2 percent.

16. A process according to claim 13 or 14, wherein the effluent gas temperature from the secondary oxygen reforming step (f) is between 900° C. and 1200° C.

17. A process according to claim 13 or 14, wherein the free oxygen-rich gas used in the secondary reforming contains less than 5 percent by volume of nitrogen and rare gases.

18. In a process for producing, from a desulfurized hydrocarbon-containing feedstock, a synthesis gas having essentially the stoichiometric composition required for methanol synthesis and low $CO_2$ content by (a) dividing said feedstock into two fractions, the first fraction representing about 30 to 66.7 percent of the total feedstock, (b) subjecting the first fraction from (a) to a primary steam reforming reaction under a high pressure, by mixing said fraction with steam, and heating the mixture thereof by indirect heat exchange, in the presence of a reforming catalyst, to form a gaseous effluent including hydrogen, (c) preheating the second fraction from (a), by indirect heat exchange and mixing said fraction with the gas effluent from (b), (d) combining effluent gas streams from (b) and (c) to obtain a gas mixture at a minimum temperature of 600° C. and containing a minimum of 35 percent methane equivalent, and (e) preheating a free oxygen-rich gas to an elevated temperature above 350° C. by indirect heat exchange; the improvement wherein the gas mixture from (d) is reacted in a single step with the oxygen rich gas from (e) in a secondary reforming reactor operating under essentially adiabatic conditions, and consisting essentially of a gas mixing zone and a reaction zone, the total amount of free oxygen injected in said mixing zone constituting the total amount of free oxygen supplied in the process for reaction with the combined effluent gas stream mixture from (d) to produce the synthesis gas and being sufficient to initiate therein the partial oxidation reaction, and the mixing of the reacting gases in said mixing zone being accomplished through a mixing apparatus designed to obtain quasi-instantaneously a homogeneous mixture before the exothermic partial oxidation reaction proceeds significantly, and with said reaction zone containing a single bed of catalyst or catalysts, whereby the total homogeneous mixture is passed only once through the whole catalyst bed thus producing a synthesis gas containing a percent methane equivalent of less than one-tenth of that of the gas mixture from (d), a $CO_2$ content of less than 8 percent by volume, and CO, $CO_2$ and $H_2$ in a stoichiometric ratio for methanol synthesis.

19. In a process for producing, from a desulfurized hydrocarbon containing feedstock, a synthesis gas having a molal $H_2/CO$ ratio below 2.5, in which after, (a) dividing said feedstock into two fractions, the first fraction representing about 5 to 40 percent of the total feedstock, (b) subjecting the first fraction from (a) to a primary steam reforming reaction under a high pressure, by mixing said fraction with steam, and heating the mixture thereof by indirect heat exchange, in the presence of a reforming catalyst, to form a gaseous effluent including hydrogen (c) preheating the second fraction from (a), by indirect heat exchange, and mixing said fraction with the gas effluent from (b), (d) combining effluent gas streams from (b) and (c) to obtain a gas mixture at a minimum temperature of 600° C. and containing a minimum of 35 percent methane equivalent, and (e) preheating a free oxygen-rich gas to an elevated temperature above 350° C. by indirect heat exchange; the improvement wherein the gas mixture from (d) is reacted in a single step with the oxygen-rich gas from (e) in a secondary reforming reactor operating under essentially adiabatic conditions, and consisting essentially of a gas mixing zone and a reaction zone, the total amount of free oxygen injected in said mixing zone constituting the total amount of free oxygen supplied in the process for reaction with the combined effluent gas stream mixture from (d) to produce the synthesis gas and being sufficient to initiate therein the exothermic partial oxidation reaction which raises the temperature of the reaction mixture, and the mixing of the reacting gases in said mixing zone being accomplished through a mixing apparatus designed to obtain quasiinstantaneously a homogeneous mixture before the partial oxidation reaction proceeds significantly, and said reaction zone containing a single bed of catalyst or catalysts, whereby the total homogeneous mixture is passed only once through the whole catalyst bed thus producing a synthesis gas containing a percent methane equivalent of less than one-tenth of that of the gas mixture from (d) and a molal $H_2/CO$ ratio below 2.5.

* * * * *